United States Patent
Greyf et al.

(10) Patent No.: US 12,097,660 B2
(45) Date of Patent: *Sep. 24, 2024

(54) IMPLANTABLE BONE SCAFFOLD PRINTED AT POINT OF SERVICE

(71) Applicant: OsseoPrint3D LLC, North Brunswick, NJ (US)

(72) Inventors: Arthur Greyf, Millburn, NJ (US); Leonid Fayn, Millburn, NJ (US)

(73) Assignee: OSSEOPRINT3D LLC, North Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/326,653

(22) Filed: May 31, 2023

(65) Prior Publication Data
US 2023/0302734 A1  Sep. 28, 2023

Related U.S. Application Data

(62) Division of application No. 16/211,224, filed on Dec. 5, 2018, now Pat. No. 11,718,034.

(Continued)

(51) Int. Cl.
*B29C 64/364* (2017.01)
*A61F 2/30* (2006.01)
(Continued)

(52) U.S. Cl.
CPC .......... *B29C 64/364* (2017.08); *A61F 2/3094* (2013.01); *B29C 64/106* (2017.08);
(Continued)

(58) Field of Classification Search
None
See application file for complete search history.

(56) References Cited

U.S. PATENT DOCUMENTS

| 2011/0012986 A1 | 1/2011 | Shikll et al. |
| 2012/0126457 A1 | 5/2012 | Abe et al. |

(Continued)

OTHER PUBLICATIONS

Effectiveness of Air Filters on Inspectapedia, Retrieved from the internet: <https://inspectapedia.com/aircond/Air_Filter_Efficiency.php>, Mar. 14, 2015, Accessed Jun. 2, 2021 (Year: 2015).

(Continued)

*Primary Examiner* — Jacob T Minskey
*Assistant Examiner* — Adrianna N Konves
(74) *Attorney, Agent, or Firm* — FOX ROTHSCHILD LLP

(57) ABSTRACT

A three dimensional (3D) printing apparatus to print an implantable bone scaffold (IBS) in an aseptic environment is described. The 3D printing apparatus includes a sterile cartridge. The sterile cartridge contains a sterile printing material, a print nozzle, and a plunger. The 3D printing apparatus also includes a heater configured to indirectly heat the printing material. In addition, the 3D printing apparatus includes a cartridge receiver configured to retain the sterile cartridge. A sterile receiving plate is positioned below the print nozzle. A cover encompasses and maintains the sterile cartridge and the sterile receiving plate in an aseptic environment. A filter fan unit (FFU) overlays a section of the cover. Positive laminar filtered air flow created by the FFU maintains the aseptic environment inside a printing chamber. An ultraviolet light source irradiates the receiving plate. A movable diaphragm separates a printer mechanism, below the receiving plate, from the printing chamber.

14 Claims, 3 Drawing Sheets

Related U.S. Application Data

(60) Provisional application No. 62/594,904, filed on Dec. 5, 2017.

(51) Int. Cl.
  *B29C 64/106* (2017.01)
  *B29C 64/20* (2017.01)
  *B33Y 10/00* (2015.01)
  *B33Y 30/00* (2015.01)
  *B33Y 40/00* (2020.01)
  *B33Y 40/10* (2020.01)
  *B29C 64/255* (2017.01)
  *B33Y 80/00* (2015.01)

(52) U.S. Cl.
  CPC .............. *B29C 64/20* (2017.08); *B33Y 10/00* (2014.12); *B33Y 30/00* (2014.12); *B33Y 40/00* (2014.12); *B33Y 40/10* (2020.01); *A61F 2002/30985* (2013.01); *B29C 64/255* (2017.08); *B29K 2995/006* (2013.01); *B33Y 80/00* (2014.12)

(56) References Cited

U.S. PATENT DOCUMENTS

| | | |
|---|---|---|
| 2015/0048257 A1 | 2/2015 | Dayton |
| 2016/0038655 A1 | 2/2016 | Weisman et al. |
| 2018/0339455 A1 | 11/2018 | Cohen et al. |

OTHER PUBLICATIONS

MERV Rating Chart, Retrieved from the internet: <http://www.mechreps.com/PDF/Merv_Rating_Chart.pdf>, Aug. 20, 10, Accessed Jun. 2, 2021 (Year: 2010).

UV Data Sheet, Retrieved from the internet: <https://www.clordisys.com/pdfs/misc/UV%20Data%20Sheet.pdf>, Oct. 2013, Accessed Jun. 2, 2021 (Year: 2013).

IMPLANTABLE BONE SCAFFOLD PRINTED AT POINT OF SERVICE

CLAIM OF PRIORITY

This application is a divisional application of patent application Ser. No. 16/211,224 filed Dec. 5, 2018, which claims the priority benefit of U.S. Provisional Patent Application No. 62/594,904, filed on Dec. 5, 2017, the contents of each of which are hereby fully incorporated by reference into this application.

FIELD OF THE EMBODIMENTS

The field of the present invention and its embodiments relate to an apparatus for producing a custom bone scaffold using three dimensional (3D) printing in an aseptic and protected enclosure.

BACKGROUND OF THE EMBODIMENTS

Bone scaffolding is possible because bone tissue, unlike most other tissues, has the ability to regenerate completely if provided the right environment, including a space into which to grow, or a matrix to grow. As native bone grows, it replaces the scaffold material, so that over time, the scaffold is replaced by a fully integrated region of new bone.

Examples of bone scaffold related mechanisms are provided below.

US Pub. 2004/0120781 pertains to a customized prosthesis, or instrument, for medical/dental applications which replicates the desired bone-graft, tooth, or tool, being replaced. A computer controlled machine cuts the desired part out of a pre-fabricated blank, directly at the site of operation.

U.S. Pat. No. 6,671,539 pertains to a workstation including a CT machine, a digital scanner, a computer, an input command mechanism, a display, and a fabricating machine.

Various systems and methodologies are known in the art. However, their structure and means of operation are substantially different from the present disclosure. The other inventions fail to solve all the problems taught by the present disclosure. At least one embodiment of this invention is presented in the drawings below and will be described in more detail herein.

SUMMARY OF THE EMBODIMENTS

The present invention and its embodiments relate to three dimensional (3D) printing apparatus to print an implantable bone scaffold (IBS). In an example embodiment of the present invention, 3D printing apparatus may include a sterile cartridge. The sterile cartridge may include a printing material, a plunger, a cylindrical body, and a print nozzle. The 3D printing apparatus may also include a heater configured to heat the printing material. In addition, the 3D printing apparatus may also include a cartridge receiver configured to retain the sterile cartridge. A sterile receiving plate may be positioned below the print nozzle. A filter fan unit may overlay a section of a cover. The positive pressure environment is created inside the printer by pushing filtered air inside the printer.

The 3D printing apparatus may print the IBS by extruding the printing material from the sterile cartridge onto the sterile plate. The printing material may not contact the 3D printing apparatus other than the sterile cartridge. As such, the printing material inside the sterile cartridge may remain sterile during a printing process. A process to heat the printing material inside the sterile cartridge may be accomplished with thermal conduction through a metal portion of the sterile cartridge. The print nozzle of the sterile cartridge may be located below the heater. As such, the print nozzle may avoid contact with any component of the 3D printing apparatus while depositing the printing material onto the sterile receiving plate.

In another embodiment of the present invention, a 3D printing apparatus to print an IBS is described. The apparatus may include a sterile cartridge. The sterile cartridge may include a printing material, a plunger, a cylindrical body, and a print nozzle. The apparatus may also include a heater configured to heat the printing material. Without contacting the material. Furthermore, the apparatus may include a cartridge receiver configured to retain the sterile cartridge. A sterile receiving plate may be positioned below the print nozzle. The sterile receiving plate may be movable and detachable. The apparatus may also include an ultraviolet light source configured to emit an ultraviolet light directed toward the sterile receiving plate and maintain an aseptic environment. The apparatus may also include a cover. The cover may be configured to encompass and maintain the sterile cartridge and the sterile receiving plate in an aseptic environment. In addition, a filter may overlay a section of the cover.

In yet another embodiment of the present invention, a method of printing an IBS with a 3D printer is described. The method may include receiving a sterile cartridge within a cartridge receiver. The sterile cartridge may include a biodegradable printing material, a plunger, a cylindrical body, and a print nozzle. A printing instruction to print the IBS may be received. A particle counter may be queried to determine a particle count within a cover encompassing the sterile cartridge and a sterile receiving plate. Next, the particle count may be received. The particle count may be determined as below a threshold. Next, an aseptic environment may be maintained within the cover by activating the ultraviolet light source and emitting an ultraviolet towards the sterile receiving plate. Furthermore, the heater may be activated to heat the biodegradable printing material. The plunger on the sterile cartridge may next be pressed to extrude the biodegradable material from the print nozzle. The IBS may be printed by moving the sterile receiving plate positioned below the print nozzle and depositing the biodegradable material on the sterile receiving plate based on the printing instruction.

It is an object of the present invention to provide a 3D printing apparatus to print an IBS.

It is an object of the present invention to provide a cartridge receiver to secure the sterile cartridge during printing.

It is an object of the present invention to provide a detachable and movable sterile receiving plate to print the IBS.

It is an object of the present invention to provide a cover that encompasses components of the 3D printing apparatus and maintains an aseptic environment. by maintaining positive pressure with filtered air.

It is an object of the present invention to maintain the aseptic environment with an ultraviolet light source, a positive airflow, and a high-efficiency particulate air (HEPA), ultra-low particulate air (ULPA), or other filter.

The mechanism is positioned below printing plate to minimize contamination

The mechanism is separated from printing bed by a diaphragm

The printer contains particle counter and software that initiates the following cycle within the printer (with a sequential methodology):
1. Sterile cartridge inserted
2. Sterile printing plate inserted
3. Printer door locks
4. Fan Activated, Laminar flow of filtered air produced in the downward (top to bottom direction)
5. Positive pressure environment created inside printing chamber
6. Particle counter activated
7. Particle counter meets required air quality
8. UV C Light activated and shines onto printing plate
9. Printing activated, the printing material is heated inside the sterile cartridge
10. Scaffold printed
11. Positive air pressure is maintained inside printer
12. UV light stays on
13. When surgeon is ready he presses unlock button
14. UV light shuts down
15. Surgeon removes the scaffold and implants it.

In addition to the foregoing, other objects features, accepts and advantages of the present invention will be better comprehended through a careful reading of a detailed description provided herein below with appropriate reference to the accompanying drawings.

DESCRIPTION OF THE PREFERRED EMBODIMENTS

Figure 1:
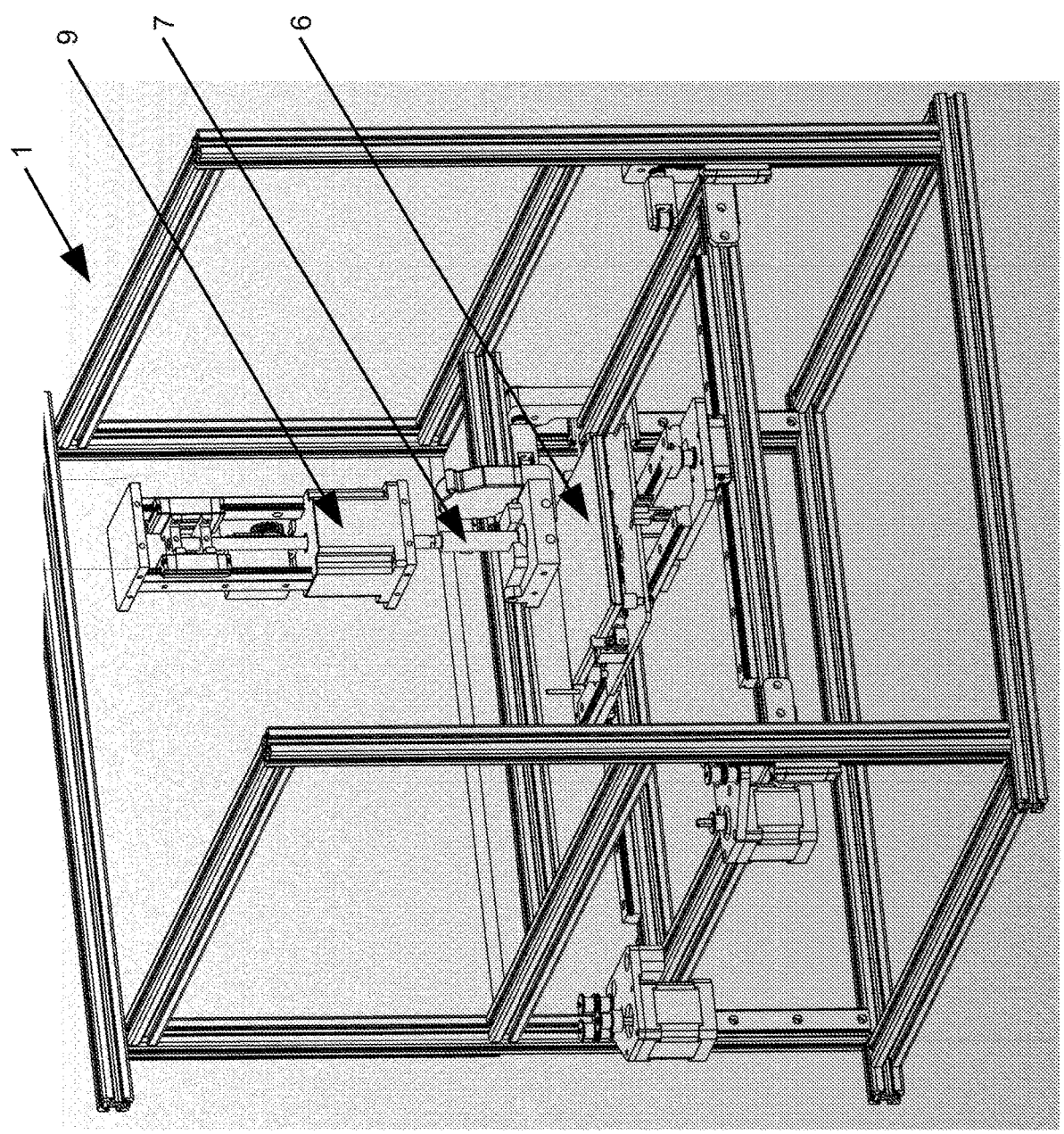
FIG. 1 shows an isometric view of an embodiment of the invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

A three dimensional (3D) printing apparatus 1 to print an implantable bone scaffold (IBS) is described. The 3D printing apparatus may provide an aseptic environment where the IBS is printed. The 3D printing apparatus 1 may be used in a number of medical fields including plastic surgery, and/or dentistry, among others. The IBS printed by the 3D printing apparatus 1 may aid in procedures, such as, but not limited to, a cleft palate surgical repair, and/or a facial and non-facial post trauma or tumor removal reconstruction, among others.

The 3D printing apparatus 1 may also be transported and situated at a medical provider such as a surgeon, and/or a dentist's office. Alternatively, the 3D printing apparatus 1 may be situated at a medical room associated with the medical provider such as a surgical room, among others. The 3D printing apparatus 1 may aid in performing an oral maxillofacial surgery, dental implants, orthopedic surgery and/or any type of reconstructive hard tissue surgery. The 3D printing apparatus 1 may reduce cost and/or time associated surgical procedures.

FIG. 1 shows an isometric view of the 3D printing apparatus 1. The 3D printing apparatus 1 may include a sterile cartridge 7. The sterile cartridge 7 may be disposable. The sterile cartridge 7 may be manufactured and sealed to maintain a sterile state until use in the 3D printing apparatus 1. The sterile cartridge 7 may include a printing material (stored in the sterile state w/in the sterile cartridge 7), a print nozzle, and a plunger. The plunger may be used by the 3D printing apparatus 1 to extrude the printing material during a printing process (to print the IBS).

The printing material may include a biodegradable material. Upon implantation of the IBS (within a biological structure of a patient), the biodegradable material may disintegrate over time and bone may grow over and replace the biodegradable material. Furthermore, the printing material may include a porous material and/or a biocompatible material. Similarly, bone may grow over (and replace) the porous and/or biocompatible printing materials.

The 3D printing apparatus 1 may also include a cartridge receiver 9. The cartridge receiver 9 may be configured to retain the sterile cartridge 7. The cartridge receiver 9 may secure the cartridge 7 upon installation by a user (such as the medical provider and/or an installation technician). Furthermore, the cartridge receiver 9 may integrate a heater. The printing material(s) may pass through the print nozzle during a printing process (to print the IBS).

The heater may heat the printing material within the cartridge 7. A temperature of the heater may be adjustable to adjust the density of the printing material.

The 3D printing apparatus 1 may also include a sterile receiving plate 6 positioned below the print nozzle. The sterile receiving plate 6 may be movable (in x, y, and/or z axis) to allow for the printing material(s) to be deposited on the sterile receiving plate 6. The movements of the sterile receiving plate 6 may form a shape of the IBS during the printing process. The sterile receiving plate 6 may also be detachable to allow for removal of the sterile receiving plate 6 and the IBS upon a conclusion of the printing process. Furthermore, the sterile receiving plate 6 may be discarded upon detaching the IBS.

Figure 2:
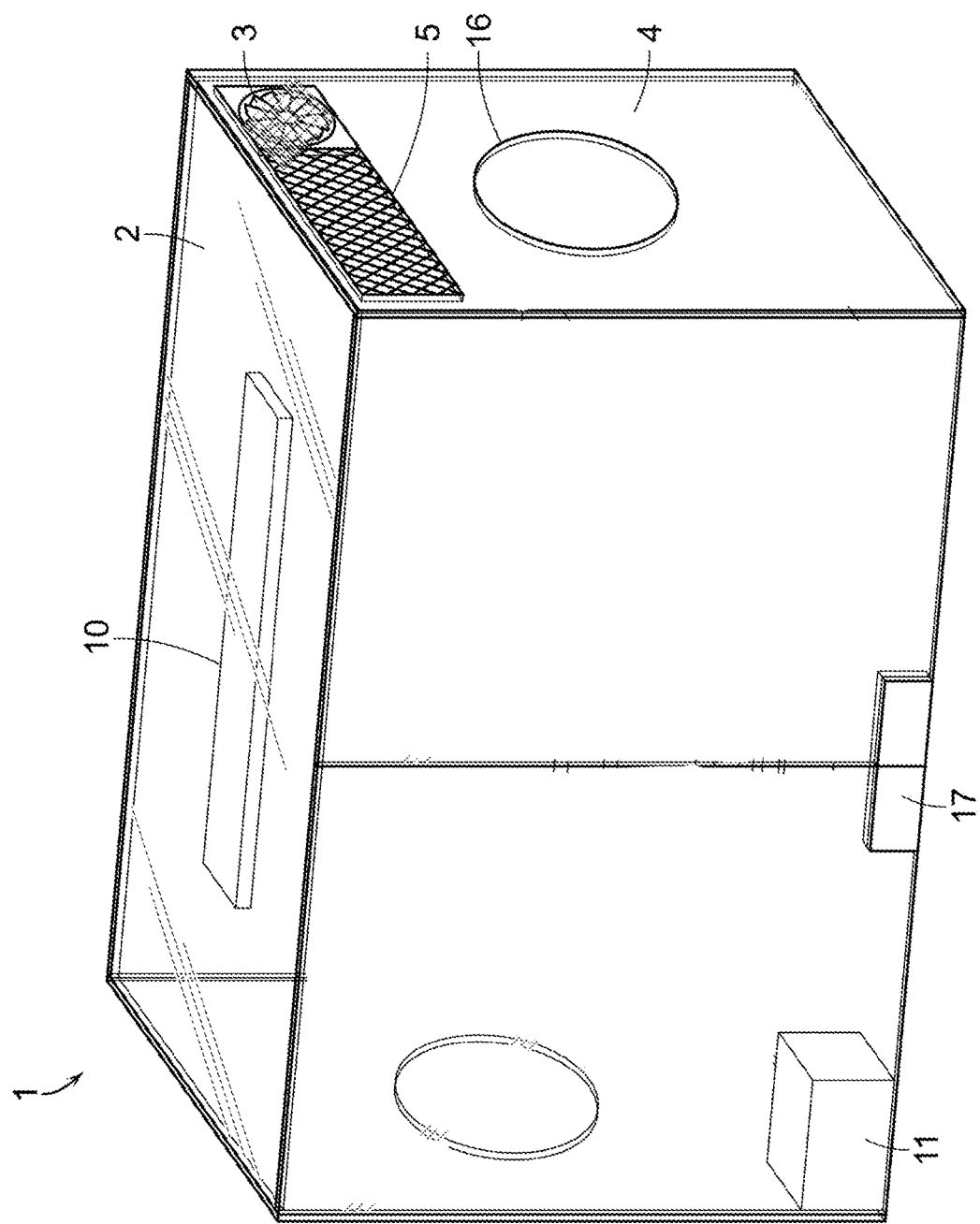
FIG. 2 shows an embodiment of the invention with a cover.

FIG. 2 shows the 3D printing apparatus 1 with a cover 2. The cover 2 may maintain an aseptic environment for the printing process. The cover 2 may also encompass the sterile cartridge 7 and the sterile receiving plate 6 in the aseptic environment. In addition, a filter fan unit (FFU) 5 may be overlaid on a top of a section 4 of the cover 2 to allow for input (and/or output) of filtered air into (and/or out of) the 3D printing apparatus 1.

The cover 2 may include a transparent material window to allow the user to see into the 3D printing apparatus 1 and to track a progress of the printing process. Furthermore, the cover 2 may include a fan 3 that builds positive laminar flow air pressure within the 3D printing apparatus 1. The positive air pressure may keep particles, and/or contaminants out of the 3D printing apparatus 1. As such, the 3D printing apparatus 1 may maintain the aseptic environment. The fan 3 may be a component of the FFU 5 integrated to the cover 2. The aseptic environment may include an environment that is free from biological microorganisms.

The FFU 5 may overlay the section 4 partially or fully. The FFU 5 may also include a filter with pores. The pores may include a diameter of less than or equal to about 0.3 μm.

The FFU 5 may allow an ingress of filtered air into and out of the 3D printing apparatus 1. The filter of the FFU 5 may overlay the fan 3.

The fan 3 may be position internal to and/or overlaying behind the filter of the FFU 5. The fan 3 may force outside air to come through the filter of the FFU 5. During the circulation of the outside air through the filter, the outside air may get sterilized (by the filter). As such, the filtered air may be circulated inside the 3D printing apparatus 1 which may create the positive laminar flow air pressure. The positive laminar flow air pressure may keep external particles outside the 3D printing apparatus 1.

Alternatively, the cover 2 may be integrated into the 3D printing apparatus 1 and may be irremovable. In such a scenario, the cover 2 may include a section that is retractable to allow for ingress into the 3D printing apparatus 1. The user may be allowed to open or close the retractable section to install, remove, or replace the sterile cartridge and/or the sterile receiving plate.

The cover 2 may also include a door to aid in ingress into the 3D printing apparatus 1 to service the components of the 3D printing apparatus 1 and/or to install/remove the sterile cartridge and/or the sterile receiving plate (to remove the IBS).

The 3D printing apparatus 1 may also include an aperture 16 to aid with ingress into the 3D printing apparatus 1. The aperture 16 may be covered with a door to maintain the aseptic environment within the 3D printing apparatus. The aperture 16 may also be covered with a glove that maintains the aseptic environment.

The 3D printing apparatus 1 may also include a particle counter 11 (placed inside the 3D printing apparatus 1). The particle counter 11 may be connected to a policy manager component. The particle counter may transmit a particle count (above a threshold) to the policy manager. The particle count above the threshold may indicate a contaminated environment. In response, the policy manager component may prevent initiation of a printing process (of the IBS). In response to another particle count below the threshold, the policy manager may allow the initiation of the printing process.

In another example scenario, the 3D printing apparatus 1 may include an ultraviolet light source 10. The ultraviolet light source 10 may emit an ultraviolet light directed toward the sterile receiving plate to kill microbiological organisms and maintain the aseptic environment. The ultraviolet light may kill or inactivate microorganisms by destroying nucleic acids and disrupting their DNA. The ultraviolet light source 10 may generate an ultraviolet light within a short wavelength range of about 265 to 280 nm. As such, the ultraviolet light source 10 may generate little or no ozone while emitting the ultraviolet light. As a result, the IBS may not be contaminated with ozone during the printing process.

A combination of the filtered air, the ultraviolet light, and the positive laminar flow air pressure within the 3D printing apparatus 1 may maintain the aseptic environment within the 3D printing apparatus 1.

In another example scenario, component(s) of the 3D printing apparatus 1 associated with a printing mechanism may be placed below the sterile receiving plate 6. The contaminant(s) ejected during a printing process may be pulled below the sterile receiving plate 6 by gravity or a laminar air flow directed from a top to a bottom of the 3D printing apparatus 1. Furthermore, the component(s) of the 3D printing apparatus 1 associated with a printing mechanism may be separated from a printing chamber with a movable diaphragm. The movable diaphragm may prevent particles generated during a printing process from entering the printing chamber.

Figure 3:
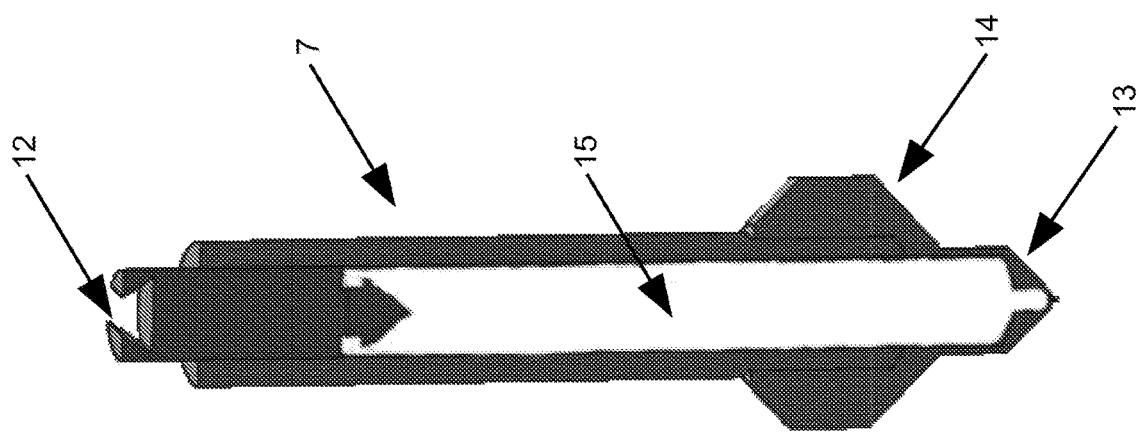
FIG. 3 shows a close up of a print nozzle of a sterile cartridge.

FIG. 3 shows a close up of the sterile cartridge 7. The sterile cartridge 7 may include a plunger 12. The sterile cartridge 7 may also include a printing material 15. The 3D printing apparatus may push the plunger 12 to extrude the printing material 15 from a printing nozzle 13. The printing nozzle 13 may deposit the printing material 15 onto a receiving plate and form the IBS based on printing instructions. The heater may apply heat to a component 14 of the sterile cartridge 7 to heat the printing material 15.

A method of printing an IBS with a 3D printer is also described. The method may include receiving a sterile cartridge within a cartridge receiver. The sterile cartridge may include a biodegradable printing material, a plunger, a cylindrical body, and a print nozzle. A printing instruction to print the IBS may be received. A particle counter may be queried to determine a particle count within a cover encompassing the sterile cartridge and a sterile receiving plate. Next, the particle count may be received. The particle count may be determined as below a threshold. Next, an aseptic environment may be maintained within the cover by activating the ultraviolet light source and emitting an ultraviolet towards the sterile receiving plate. Furthermore, the heater may be activated to heat the biodegradable printing material. The plunger on the sterile cartridge may next be pressed to extrude the biodegradable material from the print nozzle. The IBS may be printed by moving the sterile receiving plate positioned below the print nozzle and depositing the biodegradable material on the sterile receiving plate based on the printing instruction.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method to print an implantable bone scaffold (IBS) with a three dimensional (3D) printer, the method comprising:

receiving a sterile cartridge within a cartridge receiver, wherein the sterile cartridge includes a printing material, a plunger, a cylindrical body, and a print nozzle;

receiving a printing instruction to print the IBS;

querying a particle counter to determine a particle count within a cover encompassing the sterile cartridge and a sterile receiving plate;

determining that the particle count is below a threshold;

maintaining an aseptic environment within the cover during and after printing the IBS by positioning and activating an ultraviolet light source to emit sterilizing ultraviolet wavelengths onto the sterile receiving plate and the surrounding environment to produce a positive bactericidal effect;

activating a heater to indirectly heat the printing material;

pressing the plunger on the sterile cartridge to extrude the printing material from the print nozzle; and printing the IBS by moving the sterile receiving plate positioned below the print nozzle and depositing the printing material on the sterile receiving plate based on the printing instruction.

2. The method of claim 1, wherein one or more components associated with a printing mechanism are placed below the sterile receiving plate, and wherein the method further comprises pulling one or more contaminants ejected during a printing process below the sterile receiving plate by gravity or a laminar air flow directed from a top to a bottom of the 3D printer.

3. The method of claim 1, wherein one or more components associated with a printing mechanism are separated from a printing chamber with a movable diaphragm, and wherein the method further includes preventing, by the movable diaphragm, one or more particles generated during a printing process from entering the printing chamber.

4. The method of claim 2, wherein pulling the one or more contaminants comprises pulling the one or more contaminants by laminar air flow provided by a filter fan unit (FFU).

5. The method of claim 4, wherein the FFU includes pores having a diameter of less than or equal to about 0.3 μm.

6. The method of claim 4, wherein the FFU is configured to provide a positive laminar flow air pressure in a downward top to bottom direction inside the cover.

7. The method of claim 4, wherein the FFU includes a fan positioned internally to a filter of the FFU.

8. The method of claim 1, wherein the printing material includes a biodegradable material.

9. The method of claim 1, wherein the printing material includes one or more of a porous material and a biocompatible material.

10. The method of claim 1, wherein the sterile receiving plate is movable.

11. The method of claim 1, wherein the cover is one or more of transparent and detachable.

12. The method of claim 1, further comprising, in response to the particle count detected as above the threshold by the particle counter, preventing, by a policy manager component coupled to the particle counter, a start of a printing process to print the BBS.

13. The method of claim 1, wherein the sterilizing ultraviolet wavelengths are within a range of about 265 to 280 nm.

14. The method of claim 1, wherein a section of the cover is retractable.

* * * * *